United States Patent [19]

Sainte-Rose et al.

[11] Patent Number: 4,776,838

[45] Date of Patent: * Oct. 11, 1988

[54] THREE STAGE VALVE

[75] Inventors: Christian Sainte-Rose, Paris, France; Michael D. Hooven, Miami, Fla.

[73] Assignee: Cordis Corporation, Miami, Fla.

[*] Notice: The portion of the term of this patent subsequent to Dec. 2, 2003 has been disclaimed.

[21] Appl. No.: 70,680

[22] Filed: Jul. 10, 1987

Related U.S. Application Data

[63] Continuation of Ser. No. 930,048, Nov. 12, 1986, abandoned, which is a continuation of Ser. No. 672,868, Nov. 19, 1984, abandoned, which is a continuation of Ser. No. 559,392, Dec. 8, 1983, abandoned.

[51] Int. Cl.⁴ .............................................. A61M 5/00
[52] U.S. Cl. ...................................... 604/9; 604/247; 137/508; 137/504; 137/496
[58] Field of Search ................ 604/9, 10, 129, 247; 137/508, 504, 496, 503

[56] References Cited

U.S. PATENT DOCUMENTS

| | | | |
|---|---|---|---|
| 28,722 | 6/1860 | Whitacker | 137/508 |
| 79,436 | 6/1868 | Bechtel | 137/508 |
| 1,139,455 | 5/1915 | Gase | 137/508 X |
| 1,159,214 | 11/1915 | Gueux | 137/508 X |
| 1,199,152 | 9/1916 | Bruce | 137/508 |
| 1,468,434 | 9/1923 | Zauder | 137/504 |
| 2,207,382 | 7/1940 | McNamara | 277/21 |
| 2,290,151 | 7/1942 | McCollum | 237/12.3 |
| 2,969,066 | 1/1961 | Holter et al. | 128/350 |
| 3,109,429 | 11/1963 | Schwartz | 128/350 |
| 3,233,610 | 2/1966 | Wade | 128/350 |
| 3,270,771 | 9/1966 | Morgan | 137/525.3 |
| 3,288,142 | 11/1966 | Hakim | 604/9 |
| 3,308,798 | 3/1967 | Suider | 137/504 X |
| 3,492,996 | 2/1970 | Fountain | 128/350 |
| 3,566,875 | 3/1971 | Stoehr | 128/350 |
| 3,601,128 | 8/1971 | Hakim | 128/350 |
| 3,654,932 | 4/1972 | Newkirk et al. | 128/350 V |
| 3,674,050 | 7/1972 | Kuffer et al. | 137/536 |
| 3,683,929 | 8/1972 | Holter | 128/350 V |
| 3,756,243 | 9/1973 | Schulte | 128/350 V |
| 3,768,508 | 10/1973 | Schulte | 137/522 |
| 3,769,982 | 11/1973 | Schulte | 128/350 |
| 3,782,410 | 1/1974 | Steuby | 137/496 |
| 3,804,113 | 4/1974 | Garcea | 137/508 X |
| 3,827,439 | 8/1974 | Schulte et al. | 128/350 |
| 3,886,948 | 6/1975 | Hakim et al. | 128/350 V |
| 3,889,687 | 6/1975 | Harris | 128/350 V |
| 3,901,245 | 8/1975 | Spitz et al. | 128/350 V |
| 3,924,635 | 12/1975 | Hakim | 128/350 V |
| 3,970,105 | 7/1976 | Pelton | 137/504 X |
| 3,985,140 | 10/1976 | Harris | 128/350 V |
| 3,991,768 | 11/1976 | Portnoy | 128/350 |
| 3,999,553 | 12/1976 | Spitz | 128/350 |
| 4,092,999 | 6/1978 | Rubnich | 137/504 |

(List continued on next page.)

FOREIGN PATENT DOCUMENTS

68509 8/1951 Netherlands.

*Primary Examiner*—Alan Cohan
*Attorney, Agent, or Firm*—Lockwood, Alex, FitzGibbon & Cummings

[57] ABSTRACT

An implantable valve for allowing the passage of cerebrospinal fluid (CSF) from a ventricle of the brain to a suitable drainage location in the body includes a movable diaphragm, one side of which is in pressure communication with the drainage location of the body and the other side of which is in pressure communication with the ventricular spaces of the brain. A valve assembly, actuable by displacement of the diaphragm in response to a pressure differential applied thereto, regulates passage of CSF from the ventricular spaces to the drainage location. When differential pressure is relatively small, the valve is actuated to a constant pressure mode in which a predetermined differential pressure across the valve is maintained. In response to a sudden increase in differentail pressure, the valve mechanism is actuated to a constant flow mode in which a desired relatively constant rate of fluid flow is maintained. Above a predetermined pressure differential, the valve is actuated once again to a constant pressure mode in which differential pressure above a predetermined maximum is prevented.

21 Claims, 3 Drawing Sheets

U.S. PATENT DOCUMENTS

| | | | |
|---|---|---|---|
| 4,103,689 | 8/1978 | Leighton | 128/350 V |
| 4,106,510 | 8/1978 | Hakim | 604/9 |
| 4,156,422 | 5/1979 | Hildebrandt et al. | 128/748 |
| 4,167,952 | 9/1979 | Reiuicke | 137/508 X |
| 4,215,695 | 8/1980 | Spitz et al. | 128/350 |
| 4,246,930 | 1/1981 | Bishop | 137/493.9 |
| 4,332,255 | 6/1982 | Hakim et al. | 128/350 |
| 4,340,038 | 7/1982 | McKean | 128/1.3 |
| 4,437,493 | 3/1984 | Okuda | 137/504 X |
| 4,443,214 | 4/1984 | Marion | 604/9 |
| 4,452,423 | 6/1984 | Bevlavi | 251/65 |
| 4,551,128 | 11/1985 | Hakim | 604/9 |
| 4,627,832 | 12/1986 | Hooven | 604/9 |

THREE STAGE VALVE

This application is a continuation of application Ser. No. 930,048 filed Nov. 12, 1986, now abandoned, which is a continuation of application Ser. No. 672,868, filed Nov. 19, 1984, now abandoned, which is a continuation of application Ser. No. 559,392 filed Dec. 8, 1983, now abandoned.

BACKGROUND OF THE INVENTION

The present invention relates to an intracranial pressure relief valve and, more particularly, to a three stage valve which provides either constant pressure or constant flow characteristics in accordance with a fluid pressure differential applied across the valve.

Hydrocephalus is a condition in which the body, for any one of a variety of reasons, is unable to relieve itself of excess cerebrospinal fluid (CSF) collected in the ventricles of the brain. The excessive collection of CSF in the ventricular spaces results in an increase in both epidural and intradural pressures. This in turn causes a number of adverse physiological effects including compression of brain tissue, impairment of blood flow in the brain tissue and impairment of the brain's normal metabolism.

Treatment of a hydrocephalic condition frequently involves relieving the abnormally high intracranial pressure. Accordingly, a variety of CSF pressure regulator valves and methods of controlling CSF pressure have been developed which include various forms of check valves, servo valves or combinations thereof. Generally, such valves serve to divert CSF from the ventricles of the brain through a discharge line to some suitable drainage area of the body such as the venous system or the peritoneal cavity. Check valves operate by opening when the difference between CSF pressure and pressure in the discharge line exceeds a predetermined value.

One drawback to the use of a simple check valves in the treatment of hydrocephalus is that such a valve might open in response to normal variations in differential pressure between CSF ventricular pressure and pressure in the discharge line, resulting in hyperdrainage of the ventricular spaces. For example, when a patient stands after lying in a recumbent position, the differential pressure will normally increase by reason of the resulting increased ventricle height of the fluid column existing between the head and the selected drainage location. Though such an increase in differential pressure is quite normal, a check valve might respond by opening, thereby allowing undesired hyperdrainage of the ventricular spaces, which, in turn, may result in a potentially serious brain hematoma. Accordingly, it is desirable to provide a hydrocephalus pressure relief valve which is effective in shunting CSF in response to abnormal intracranial pressures while avoiding hyperdrainage in the event of normal variations in body fluid pressures.

The present invention is directed to a pressure relief valve which prevents the excessive flow of CSF in the event of sudden increases in differential pressure. In such a valve, the differential pressure between CSF and fluid in the drainage location acts to displace a movable area of a diaphragm. Such movement of the diaphragm actuates a valve regulating the passage of CSF to the drainage area. When the pressure differential is relatively small, the valve allows the passage of fluid at a flow rate sufficient to maintain a desired ventricular CSF pressure. However, a sudden increase in differential pressure, as would occur when the patient stands, causes the valve to operate essentially as a constant flow device in which passage of fluid is maintained at a relatively constant desired flow rate. A very high differential pressure, as might occur as a result of undesired clogging of the valve, causes the valve to once again operate in a constant pressure mode this time at a higher pressure, thereby preventing CSF pressure from building above a predetermined maximum safe value.

In view of the foregoing, it is a general object of the present invention to provide a new and improved pressure regulator valve for relieving intracranial pressure caused by the presence of excess CSF in the ventricles of the brain.

It is a more specific object of the present invention to provide a pressure regulator valve which avoids undesired hyperdrainage of the ventricular spaces as a result of normal increases in differential pressure.

SUMMARY OF THE INVENTION

A valve for controlling the passage of body fluids from one location in the body to another location includes a housing having first and second interior chambers. An inlet port establishes fluid communication between the first chamber and the one location while an outlet port establishes fluid communication between the second chamber and the other location. A valve mechanism between the first chamber and the second chamber regulate the passage of fluid between the chambers. The valve may be actuated to any one of four conditions. In the first of these conditions, fluid communication between the first and second chambers is prevented. In the second condition fluid communication is provided between the first and second chambers at a flow rate sufficient to maintain a desired constant first pressure differential between the first and second chambers. In the third condition, fluid communication is provided between the first and second chambers sufficient to maintain a desired relatively constant flow rate of fluid between the chambers while in the fourth condition fluid communication between the chambers is provided at a fluid flow rate sufficient to maintain a constant desired second pressure differential between the first and second chambers. The valve includes partition means in the housing which include a movable member separating the first and second chambers and which moves in response to the pressure differential therebetween. The movable member is associated with the valve mechanism such that motion of the member in response to an increasing pressure differential between fluids in the first and second chambers sequentially conditions the valve mechanism from the first condition through the second and third conditions to the fourth condition. Accordingly, the valve mechanism will be sequentially conditioned to one of the four conditions in response to an increasing pressure differential between fluid at the one location of the body and fluid at the other location of the body.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

DESCRIPTION OF THE PREFERRED EMBODIMENT

Figure 1:
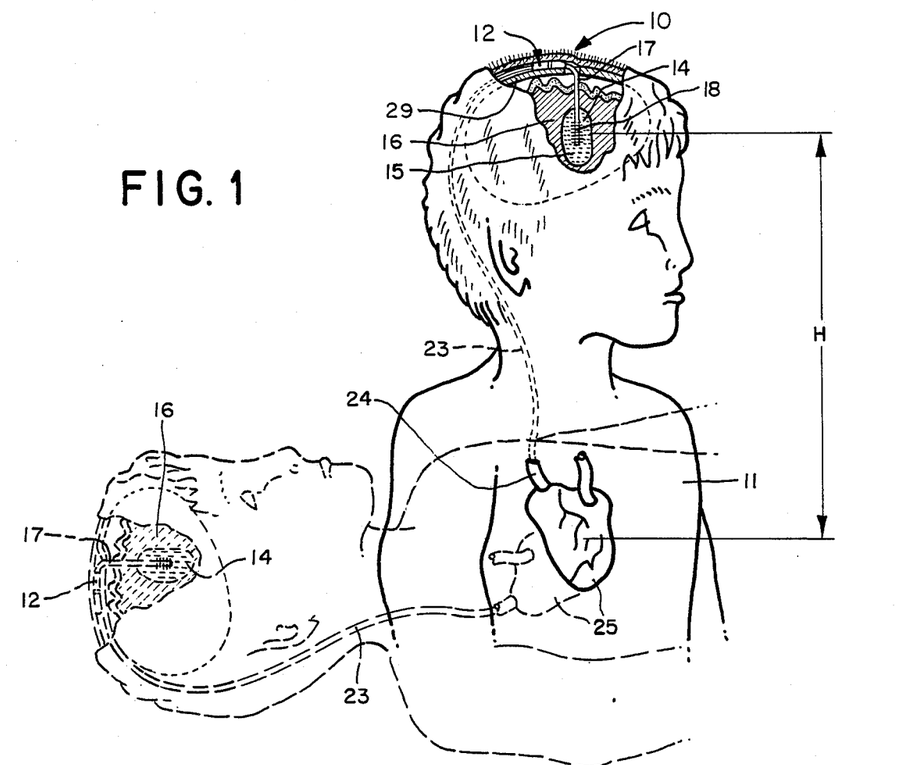
FIG. 1 is a perspective view, partially in section, of a hydrocephalus system employing a three stage pressure regulator valve constructed in accordance with the invention, showing such a system implanted within a patient.
Figure 2:
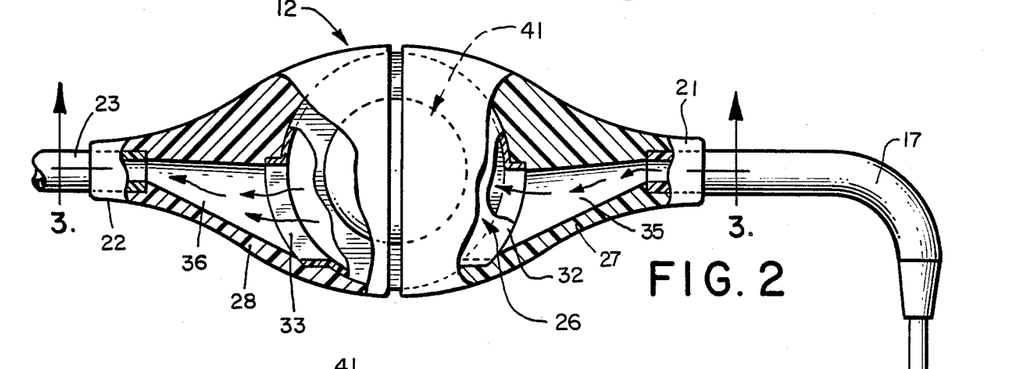
FIG. 2 is a plan view, partially in section, of a hydrocephalus system showing the principal elements thereof.

Referring to the drawings, and particularly to FIG. 1, a hydrocephalus system 10 for maintaining a desired predetermined intracranial pressure in a patient 11 is illustrated. The system shown includes a three stage pressure relief valve 12 constructed in accordance with the present invention for maintaining the desired intracranial pressure.

Cerebrospinal fluid (CSF) 14 is drained from a ventricle 15 of the brain 16 by means of a ventricular catheter 17. Preferably, the catheter is radio-opaque in order to facilitate its accurate placement within the brain. The distal end 18 of the catheter is provided with a plurality of apertures 20 allowing the passage of CSF therethrough and is positioned in a suitable brain ventricle as illustrated. The other end of the catheter is coupled to the inlet port 21 of the valve thereby establishing fluid communication between the valve and the ventricle. The outlet port 22 of the valve is attached to one end of a drain catheter 23, the opposite end of which discharges into an appropriate location of the patient's body. As illustrated, the drain catheter is threaded through an appropriate vein 24 to terminate within the right atrium of the heart 25. Another drainage location, for example, the peritoneal cavity, could also be selected. When open, the valve allows passage of CSF from the brain ventricles to the selected discharge location thereby relieving CSF pressure caused by excessive accumulation of CSF.

Normally, a pressure differential exists between CSF within the ventricle and fluid in the selected drainage location. Accordingly, a differential pressure will exist between fluids applied to the inlet and outlet ports of the valve. The valve illustrated is of the type which opens when the pressure differential exceeds a predetermined threshold value. Typically, the valve 12 includes means for adjusting the differential pressure threshold at which it opens so that the hydrocephalus system may be adjusted to suit the specific requirements of an individual patient.

While an increased differential pressure may result from the excessive accumulation of CSF in the brain ventricles, such an increase may be a perfectly normal response to ordinary physical activity of the patient. For example, when a patient stands after lying for some time in a recumbent position as illustrated in phantom in FIG. 1, the differential pressure will suddenly increase by reason of the sudden increase in vertical height H of the fluid column existing between the distal end of the ventricular catheter 17 and the drainage location. If the relief valve were to open and permit unrestrained fluid flow during this period, hyperdrainage of the ventricle, and a drain hematoma, are possible results. Accordingly, the valve includes means for preventing such unrestricted fluid flow to the drainage location in the event of a sudden increase in the differential pressure.

The internal construction and operation of the three stage valve may best be understood by reference to FIGS. 2-6. As illustrated, the valve includes a disc-shaped inner housing 26 fashioned from a durable, biologically compatible material, such as thermoplastic polymers of polyethersulfone or polycarbonates. The inner housing 26 is received within an outer housing comprising two members 27 and 28 formed of silicone rubber or similar material bonded together over the inner housing. The dimensions of the inner and outer housings are selected so as to be compatible with subcutaneous implantation of the valve over the cranium 29.

Figure 3:
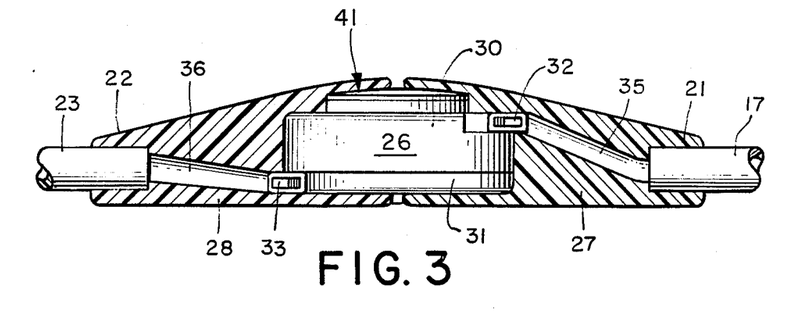
FIG. 3 is a cross sectional view taken along line 3—3 of FIG. 2.
Figure 4:
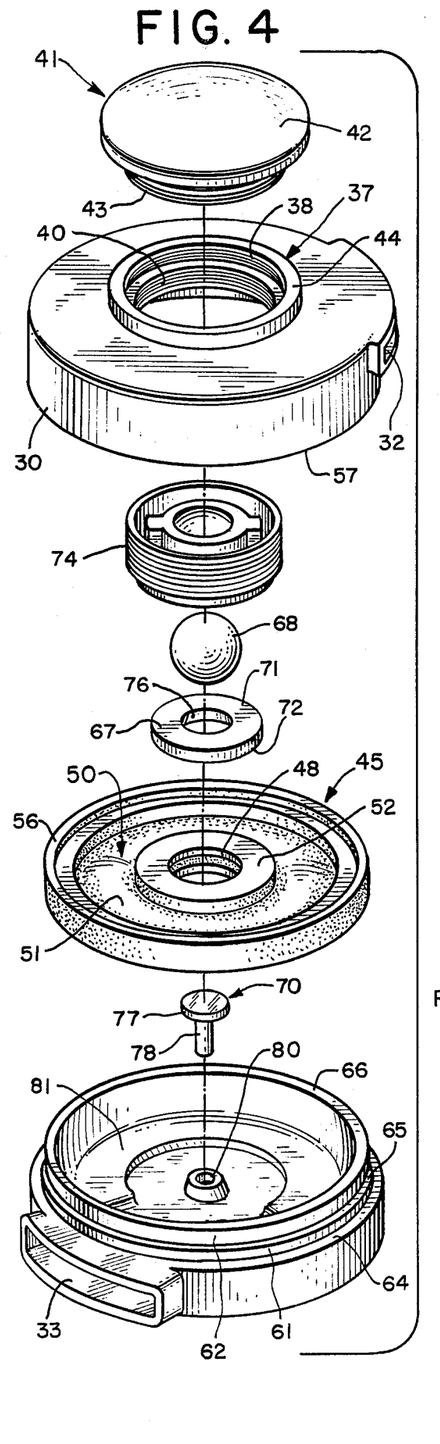
FIG. 4 is an exploded perspective view of a three stage pressure regulator valve constructed in accordance with the invention showing the principal elements thereof.
Figure 5:
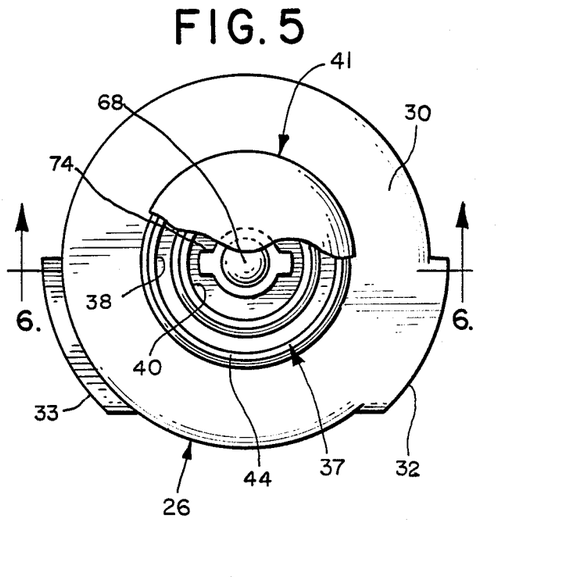
FIG. 5 is a plan view, partially in section, of the three stage pressure regulator valve shown in FIG. 4.

As is best illustrated in FIGS. 3 and 4, the inner housing includes two circulat cup-shaped members 30 and 31, each including a single port 32 and 33 respectively, by means of which fluid can pass to or from the interior region of the housing. In this regard, outer ousing members 27 and 28 are provided with internal conduits 35 and 36 respectively, which allow fluid communication between the inlet and outlet ports and the housing 26.

Upper housing member 30 is provided with an aperture 37 through the upper surface thereof. As illustrated, the aperture 37 includes a region of relatively larger diameter 38 coaxially aligned above a region of relatively smaller diameter 40. Both the relatively larger diameter and smaller diameter regions of the aperture are internally threaded as illustrated. In order to seal the aperture while still allowing ready access to the interior region of the housing, the upper housing member 30 also includes a removable cap 41 having a domed upper surface 42 and an externally threaded cylindrical lower portion 43 dimensioned as to engage the threads of the relatively larger diameter segment 38 of the aperture 37. To allow a tight seal between the cap and the housing, the upper housing member includes a raised annular seat 44 adjacent the periphery of the aperture against which the cap bears as it is screwed into the upper housing member.

Figure 6:
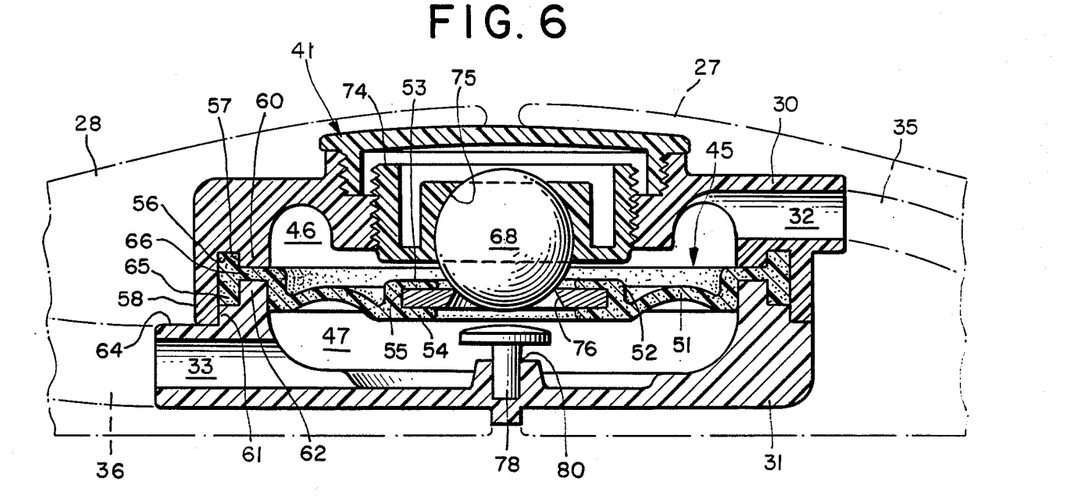
FIG. 6 is an enlarged cross-sectional view of the valve shown in FIG. 5 taken along line 6—6 thereof.

Referring further to FIGS. 3 and 4, the valve includes partition means in the form of a movable member or diaphragm 45 extending laterally across the interior region of the inner housing thereby dividing that region into first and second interior chambers 46 and 47, respectively. The diaphragm 45 is fashioned from a flexible biocompatible material, such as silicone rubber, and, as best seen in FIG. 3, comprises a disc-shaped member having an aperture 48 provided centrally therethrough. The operative surface 50 of the diaphragm is provided with an annular groove 51 concentrically aligned with the center aperture which allows the operative surface to travel vertically in response to differential pressure across the diaphragm such as might result from a difference in pressures in the first and second interior chambers. Toward its center, and in the region immediately surrounding the aperture, the thickness of the diaphragm is increased to form a raised area 52, while both the upper and lower surfaces of the raised area, 53 and 54 respectively, are undercut to form a circular, rectangular cross-sectioned channel 55 therebetween as is best seen in FIG. 6. The diaphragm 45 also includes an integrally formed raised circular edge 56 projecting both above and below the operative surface 50 along its outer circumference. This edge, in a manner to be developed, facilitates installation of the diaphragm within the housing.

The manner in which the diaphragm is held in position relative to both the upper and lower housing members is best illustrated in FIGS. 4 and 6. Referring to those Figures, it will be seen that the lower edge of the upper housing member is provided with a rectangular cross section channel 57 thereby forming inner and outer sleeves 58 and 60 respectively. As illustrated, the vertical dimension of the inner sleeve 58 is less than that of the outer sleeve 60 while the channel 57 is dimensioned to receive the outer raised edge 56 of the diaphragm. The upper edge surface of the lower housing member is provided with a pair of raised steps 61 and 62 thereby forming concentric annular ledges 64, 65 and 65 thereon. When assembled, the lower edge of the outer sleeve 60 contacts the first ledge 64, while the second ledge 65 is dimensioned so as to contact the lower edge 56 of the diaphragm when the diaphragm is in place. Similarly, the inner ledge 64 is dimensioned as to allow the diaphragm to be received in the space formed between the upper edge thereof and the lower edge of the interior sleeve 60. Thus, when assembled, upper housing member 30 interlocks with lower housing member 31 by engagement of their corresponding edges, while the diaphragm 45 is received in the spaced provided therebetween thereby rigidly affixing the outer periphery of the diaphragm relative to the two interior housing members. When mounted in this manner, the operative surface 50 of the diaphragm is free to travel vertically in response to a pressure differential existing between fluids contained in the first and second chambers.

To regulate the passage of fluid from the first chamber 46 to the second chamber 47 and hence from a brain ventricle to the selected drainage area of the body, the valve includes valving means for regulating fluid communication between the first and second chambers. Such valving means take the form of a valve seat 67 mounted for movement between valve closure means and fluid restrictor means. In the embodiment illustrated, such valve closure means take the form of a sphere 68, fashioned from ruby, sapphire or similar hard, biocompatible material, while the fluid restrictor means take the form of a generally cylindrical restrictor 70 also fashioned from ruby, sapphire or similar such material. The valve seat 67, formed of the same material selected for the sphere and the restrictor, comprises a disc having flat, parallel, upper and lower faces 71 and 72. As is best seen in FIG. 6, the valve seat is received within the channel 55 formed in the raised segment 52 of the diaphragm adjacent the aperture provided centrally therethrough whereby the valve seat travels with movement of the diaphragm. The ruby valve closure sphere 68 is positioned directly above the valve seat and is held in position by means of a cylindrical collar 74 externally threaded and dimensioned to engage the threads of the relatively narrow diameter segment 40 of the aperture provided in the upper surface of upper housing member 30 directly beneath the cap 41. The cylindrical collar 74 includes a central hollow region 75 dimensioned to receive the ruby sphere 68 and may be engagingly or disengagingly rotated relative to the upper housing member whereby the vertical position of the sphere relative to the valve seat 67 may be adjusted. As may further be seen in FIG. 6, the valve seat 67 includes an orifice 76 extending centrally therethrough which provides fluid communication between the first and second chambers. As illustrated, the orifice 76 is located directly beneath the sphere 68 so that when the sphere contacts the upper surface of the valve seat 67, as would occur when the diaphragm 45 is deflected upwardly, it totally occludes the orifice thereby precluding the passage of fluid between the first and second chambers. The restrictor extends perpendicularly upward from the lower interior surface of the inner housing and is positioned directly beneath the valve seat orifice so that downward travel of the diaphragm and the valve seat results in the introduction of the restrictor 70 into the orifice thereby partially occluding the passage between the first and second chambers.

It will be observed that the orifice 76 provided in the valve seat is not a simple cylindrical aperture but rather is tapered so that the orifice 76 is narrowest at the upper surface 71 of the valve seat 67 and widest at its lower surface 72. The restrictor 70 is generally cylindrical in form and includes a segment of relatively larger diameter 77 above and coaxially aligned with a segment of relatively narrower diameter 78 the lower edge of which is received in a suitable recess 80 provided in the lower interior surface of housing member 31 thereby affixing the restrictor perpendicularly relative to that surface. The dimension of the restrictor is selected so that it will barely pass through the orifice at its narrowest point. By way of example, in one embodiment of the valve, the valve seat orifice had a diameter of 0.040 inches at its narrowest point and the clearance between the restrictor and the orifice at the narrowest point was on the order of 0.001 inches.

Figure 8:
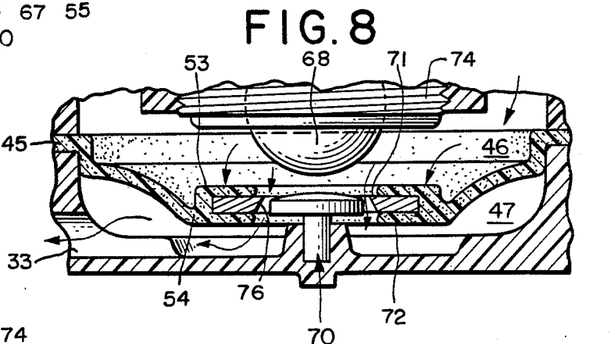
FIG. 8 is a cross-sectional view, similar to FIG. 6, showing the valve in a constant flow-rate mode.
Figure 9:
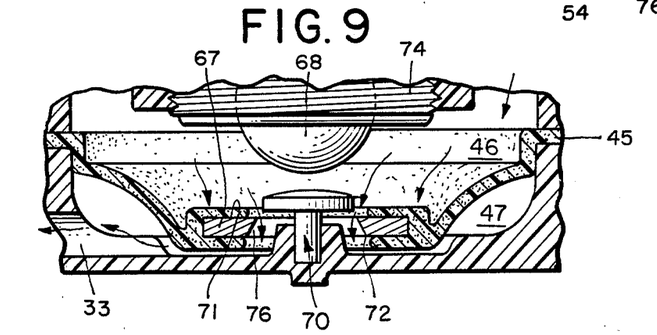
FIG. 9 is a cross-sectional view, similar to FIG. 6, showing the valve in a second constant pressure mode.
Figure 10:
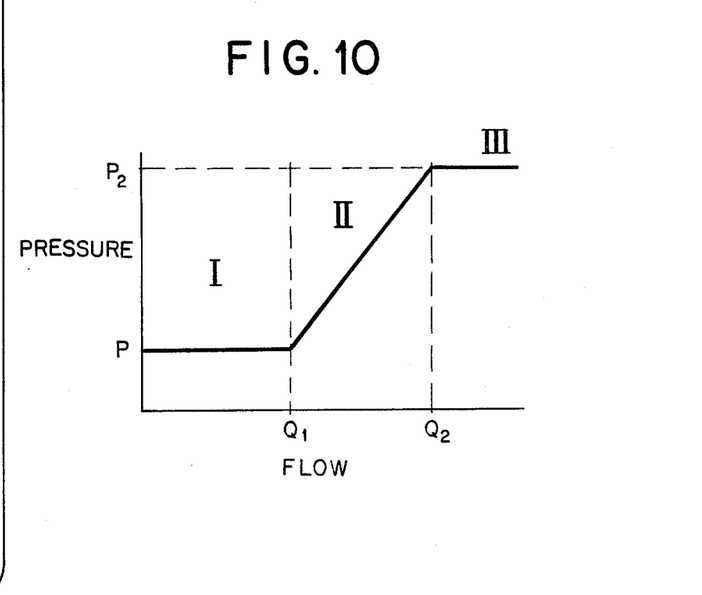
FIG. 10 is a graphical representation of certain pressure and flow characteristics of the three stage valve construction in accordance with the invention useful in understanding the operation thereof.

The operation of the valve may best be understood by reference to FIGS. 6-10 and the description which follows. FIG. 10 is a graphical depiction of pressure versus flow characteristics of a valve constructed in accordance with the invention. Briefly, the valve operates to maintain a desired differential pressure $P_1$ between fluids in the brain ventricles and at the selected discharge location of the body. The valve accomplishes this by adjusting the fluid flow rate Q so that the desired pressure $P_1$ is maintained. Such operation of the valve occurs within the region designated I on the graph of FIG. 10.

When differential pressure rapidly increases, such as when the patient stands, a flow rate greater than a preselected rate $Q_1$ will be necessary to maintain the desired first pressure $P_1$. However, such a flow rate may create risks of undesirable hyperdrainage of the brain ventricles. Accordingly, when such a rapid increase in differential pressure occurs, the valve automatically serves to maintain a relatively constant desired rate of fluid flow despite changes in differential pressure. In a practical valve, the flow rate will not be entirely independent of the applied differential pressure but rather will increase from a lower flow rate $Q_1$ to a higher flow rate $Q_2$ as differential pressure increases between first pressure $P_1$ and a second pressure $P_2$ as indicated by the solid line in FIG. 10. A valve operating in this condition is operating in region II of FIG. 10. Flow rates $Q_1$ and $Q_2$ are sufficiently low so that during a temporary rapid increase in differential pressure, pressure will return to normal before a quantity of CSF sufficient to cause adverse side effects may flow through the valve. In a typical valve $Q_1$ and $Q_2$ might be 0.4 ml./min and 0.8 ml./min. respectively, while first and second pressures, $P_1$ and $P_2$ may have values of 80 and 350 millimeters of water respectively.

While it is desirable to avoid high flow rates through the valve in order to avoid hyperdrainage of the ventricles, it may, under certain emergency conditions, be desirable to allow rapid shunting of CSF in order to avoid possible brain damage. When the valve is operating in region II, increases in differential pressure tend to close the valve between the first and second interior chambers. To avoid the possibility of building extremely high ventricular CSF pressure, the valve is constructed so that when differential pressure exceeds a second pressure $P_2$ substantially higher than first pressure $P_1$, the valve once again operates to allow a fluid flow rate sufficient to maintain a differential pressure no higher than second pressure $P_2$. Such operation is that which would occur in region III of FIG. 10. When the valve is operating in this region, further increases in differential pressure result in an increase in fluid flow through the valve thereby stabilizing differential pressure.

Figure 7:
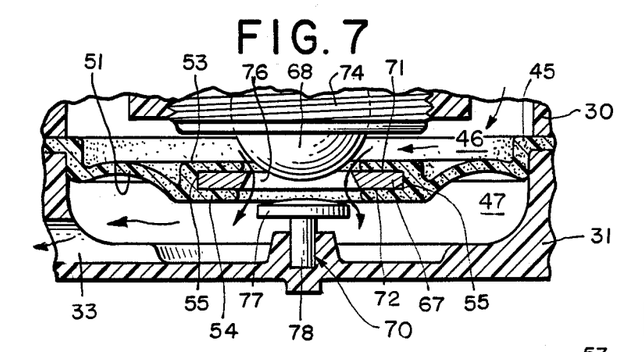
FIG. 7 is a cross-sectional view, similar to FIG. 6, showing the valve in a first constant pressure mode.

FIGS. 6-9 illustrate operation of the valve in each of the regions previously described. CSF applied to the inlet port 21 of the valve completely fills the first chamber 46 and exerts a downwardly directed force on the diaphragm 45 by reason of the CSF pressure within the brain ventricle. Since the second chamber 47 is in fluid communication with the selected drainage location in the body, the pressure of the CSF therein exerts an upwardly directed force on the lower surface of the diaphragm. Accordingly, the differential pressure between CSF in the brain ventricle and fluid at the drainage location results in verticle deflection of both the diaphragm and the valve seat 67 rigidly attached thereto. As shown in FIG. 6, when valve seat 67 contacts sphere 68, the orifice 76 is totally occluded, thereby preventing fluid flow between chambers 46 and 47. When differential pressure is relatively low, such as when the valve is operating in region I FIG. 10, the resulting slight downward displacement of the diaphragm is sufficient to displace the valve seat 67 relative to the sphere 68 thereby allowing fluid to pass through the orifice 76 from the first interior chamber 46 to the second interior chamber 47. The valving means in this condition are illustrated in FIG. 7. As shown, downward deflection of the diaphragm is sufficient to allow the passage of fluid through the orifice, yet the upper surface of the restrictor 70 is sufficiently removed from the orifice so as not to interfere with the flow of fluid between the chambers. In this condition, the valve acts primarily as a constant presure device whereby a constant pressure differential is maintained between the fluids in the first and second chambers. A slight increase in differential pressure results in slight downward deflection of the diaphragm thereby further opening the valve means to allow greater fluid flow between the chambers with the results that the increased pressure in the first chamber is rapidly relieved. Similarly, a decrease in the pressure of fluid in the first chamber allows the diaphragm to move toward the sphere, thereby restricting the fluid flow between the chambers, thus allowing pressure in the first chamber to increase.

FIG. 8 illustrates the condition of the valve when a sudden increase in differential pressure is applied to the valve. When such an event occurs, the pressure differential exceeds the first desired pressure $P_1$ and consequently the valve operates in region II of FIG. 10. When such a differential pressure is applied to the valve, the downward displacement of the diaphragm 45 is sufficient to cause the valve seat 67 to descend over the restrictor 70 thereby causing the restrictor to partially occlude the orifice 76 therein. Because the orifice is tapered, additional downward travel of the valve seat results in a further occlusion of the orifice. The orifice is shaped such that the additional occlusion occuring orifice by reason of increasing differential pressure is sufficient to offset the higher flow rate ordinarily resulting from increased pressure thereby resulting in a relatively uniform rate fluid flow between the chambers despite increase in differential pressure. Accordingly, in this condition, the valve acts primarily as a constant flow device permitting the passage of fluid from the first to the second chamber at a relatively constant desired rate despite changes in applied differential pressure.

FIG. 9 illustrates operation of the valve in region III of FIG. 10 such as would occur when differential pressure exceeds the desired second pressure $P_2$. In this condition, differential pressure displaces the diaphragm to a degree sufficient to cause the large diameter end 77 of the restrictor 70 to protrude past the upper surface of the valve seat thereby allowing fluid to easily flow past the restrictor and through the orifice 76. It will be noted, that in this condition, the orifice is not nearly as restricted as it was in FIG. 8 when the large diameter end of the restrictor 70 was received within the tapered region of the valve seat 67. When the valve is operating in this manner, increases in differential pressure cause the valve seat to be further displaced away from the restrictor, thereby further opening the orifice, and allowing a greater fluid flow rate. Thus, the valve once again operates essentially as a constant pressure device whereby differential pressure greater than a desired maximum pressure $P_2$ is prevented. A further advantage of this construction, is that as the restrictor passes through the orifice, it tends to remove foreign materials which may tend to clog the valve. Thus, should clogging occur, the resulting increased differential pressure will eventually cause the restrictor to pass through the orifice thereby providing the valve with a self-cleaning feature.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. A surgically implantable valve for controlling the passage of cerebrospinal fluid from a ventricle in the brain, wherein the fluid is normally subject to pressure variations within a predetermined nominal range, and abnormally subject to pressure variations in excess thereof extending to a predetermined maximum allowable level, to a drain location in the body which is of a relatively constant pressure, comprising:

a housing having first and second interior chambers;

inlet port means for establishing fluid communication between said first interior chamber and the source location;

outlet port means for establishing fluid communication between said second interior chamber and the drain location;

valving means for regulating fluid flow between said first and second chambers, said valving means providing a first condition in which fluid flow between said first and second chambers is prevented, a second condition in which fluid flow between said first and second chambers is regulated to maintain a first substantially constant predetermined pressure in said first chamber, a third condition in which fluid flow between said first and second chambers is maintained at a substantially constant rate, and a fourth condition in which fluid flow between said first and second chambers is regulated to maintain a second substantially constant predetermined pressure in said first chamber; and valve actuator means in said housing, responsive to the pressure differential between said first and second interior chambers for substantially actuating said valving means from said first condition through said second and third conditions to said fourth condition whereby, in response to an increasing pressure differential between fluid at the source location and fluid at the drain location, said valving means in said first condition prevents the passage of fluid between the source location and the drain location when the source pressure falls below the nominal range, said valving means in said second condition maintains a constant fluid pressure differential between the source location and the drain location when the source pressure is in the nominal range, said valving means in said third condition maintains a desired constant rate of fluid flow between the source location and the drain location when the source pressure is greater than the nominal range but less than the maximum allowable level, and said valving means in said fourth condition maintains said maximum allowable pressure level at the source location.

2. A surgically implantable valve as defined in claim 1 wherein said valving means further comprise:

valve closure means mounted within said housing; and fluid flow restrictor means mounted in said housing opposite said valve closure means and spaced apart therefrom.

3. A flow regulating valve as defined in claim 2 wherein said valve actuator means comprise a diaphragm separating said first and second chambers.

4. A flow regulating valve as defined in claim 3 wherein said valve seat means are carried on said diaphragm.

5. A surgically implantable valve as defined in claim 2 wherein said valve closure means comprise a spherical surface.

6. A surgically implantable valve as defined in claim 5 wherein said fluid flow restrictor means comprise a generally cylindrical member mounted to an interior surface of said housing.

7. A surgically implantable valve as defined in claim 6 wherein said orifice is tapered such that the narrowest region of said orifice is nearest said valve closure member and the widest region of said orifice is nearest said cylindrical member.

8. A surgically implantable cerebrospinal fluid control valve for regulating the passage of cerebrospinal fluid from a source location in the brain to a drain location in the body, wherein the cerebrospinal fluid is normally subject to pressure variations within a predetermined nominal range, and abnormally subject to pressure variations in excess thereof extending to a predetermined maximum allowable level, comprising:

a bio-compatible housing;

means including a flexible diaphragm within said housing for dividing the interior thereof into first and second interior chambers, said diaphragm including a central portion having a position within said housing dependent on the fluid pressure differential between said chambers;

a bio-compatible valve seat forming a part of said central portion of said diaphragm for movement therewith and defining a passageway opening from said first interior chamber into said second interior chamber;

inlet port means for communicating said first interior chamber with cerebrospinal fluid from the source location;

outlet port means for communicating cerebrospinal fluid from said second interior chamber to the drain location in the body;

bio-compatible valve closure means in said first interior chamber arranged for operative association with said valve seat upon positioning of said diaphragm in response to the fluid pressure differential between said first chamber and said second chamber falling below a first predetermined threshold level corresponding to the minimum nominal source pressure to establish a first valving condition by closing said passageway to prevent fluid flow between said first and second chambers; and bio-compatible fluid flow restrictor means mounted within said housing and in operative association with said valve seat throughout multiple positioning of said diaphragm in response to said pressure differential, said restrictor means with said valve seat to provide a second valving condition wherein a first predetermined pressure differential is maintained when the source pressure is within the nominal range, a third valving condition wherein a constant flow rate is maintained when the source pressure is greater than the nominal range but less than the maximum level, and a fourth valving condition wherein a second predetermined pressure differential is maintained when the source pressure equals the maximum allowable level.

9. A surgically implantable cerebrospinal fluid control valve as defined in claim 8 wherein said passageway is of generally circular cross section and is tapered such that the narrowest region of said passageway faces said first interior chamber and the widest region of said passageway faces said second interior chamber.

10. A surgically implantable cerebrospinal fluid control valve as defined in claim 9 wherein said fluid flow restrictor means are dimensioned to pass through said narrowest region of said passageway.

11. A surgically implantable cerebrospinal fluid control valve as defined in claim 10 wherein said fluid flow restrictor means enters said widest region of said passageway when said pressure differential exceeds said first predetermined threshold and exits said narrowest region when said pressure differential exceeds a second higher predetermined threshold.

12. A surgically implantable cerebrospinal fluid control valve as defined in claim 11 wherein the taper of said passageway and the dimension of said restrictor means are such that the rate of fluid flow through said passageway is substantially constant when said pressure differential is greater than said first predetermined threshold and less than said second higher predetermined threshold.

13. A surgically implantable cerebrospinal fluid control valve as defined in claim 12 wherein said valve further comprises adjustment means for adjusting the position of said valve closure means relative to said diaphragm such that said first predetermined threshold level can be adjusted.

14. A surgically implantable cerebrospinal fluid control valve for controlling the passage of cerebrospinal fluid from one location in the brain to another location in the body, comprising:
a housing having first and second interior chambers;
inlet port means for establishing fluid communication between said first chamber and the one location;
outlet port means for establishing fluid communication between said second chamber and the other location;
valving means for regulating fluid flow between said first and second chambers, said valving means providing a first condition in which fluid flow between said first and second chambers is prevented, a second condition in which fluid flow between said first and second chambers is sufficient to maintain a first substantially constant predetermined pressure in said first chamber, a third condition in which fluid flow between said first and second chambers is of a substantially constant rate, and a fourth condition in which fluid flow between said first and second chambers is sufficient to maintain a second substantially constant predetermined pressure in said first chamber;
partition means in said housing including a diaphragm separating said first and second chambers and movable in response to the pressure differential therebetween, said diaphragm being operatively associated with said valving means such that motion of said diaphragm in response to an increasing pressure differential between fluids in said first and second chambers sequentially conditions said valving means from said first condition through said second and third conditions to said fourth condition whereby in response to an increasing pressure differential between fluid at the one location and fluid at the other location, the valve sequentially prevents the passage of fluid between the one location and the other location, maintains a constant fluid pressure differential between the one location and the other location, maintains a desired constant rate of fluid flow between the one location and the other location, and maintains a second constant fluid pressure differential between the one location and the other location; and
said valving means further comprising valve closure means mounted within said housing, fluid flow restrictor means comprising a generally cylindrical member mounted in said housing and aligned with said valve closure means, and valve seat means forming a part of said diaphragm and having an orifice therethrough, said orifice being dimensioned as to allow the passage of said restrictor means therethrough, said valve seat means being positioned relative to said valve closure means and said restrictor means and mounted for movement by said diaphragm from said first condition in which said valve seat means move into closing relationship with said valve closure means, to said second, third and fourth conditions in which said restrictor means approach and extend into said orifice of said valving means to partially restrict fluid flow therethrough.

15. A surgically implantable cerebrospinal fluid control valve as defined in claim 14 wherein said orifice is a frusto-conical configuration presenting a progressively increasing diameter toward said restrictor means.

16. A surgically implantable cerebrospinal fluid control valve as defined in claim 14 wherein said valve closure means include a spherical surface directed towards said valve seat means.

17. A surgically implantable cerebrospinal fluid control valve as defined in claim 14 wherein said valve closure means are adjustable toward and away from said valve seat means.

18. A surgically implantable cerebrospinal fluid control valve as defined in claim 15 wherein said valve closure means are adjustable toward and away from said valve seat means.

19. A surgically implantable cerebrospinal fluid control valve for controlling the passage of cerebrospinal fluid from one location in the body to another location, comprising:
a housing having first and second interior chambers;
inlet port means for establishing fluid communication between said first chamber and the one location;
outlet port means for establishing fluid communication between said second chamber and the other location;
valving means in said housing to control passage of body fluids between said first and second chambers, said valving means including a valve seat means and at least one fluid flow restrictor means with at least one of said valving means being movable relative to at least another of said valving means into and out of positions which establish a first condition in which fluid communication between said first and second chambers is prevented, a second condition in which fluid communication is provided between said first and second chambers at a flow rate sufficient to maintain a substantially constant desired first pressure in said first chamber, a third condition in which fluid communication is provided between said first and second chamber sufficient to maintain a desired substantially constant flow rate of fluid between said first and second chambers, and a fourth condition in which fluid communication is provided between said first and second chambers at a flow rate sufficient to maintain a substantially constant desired second pressure in said first chambers; and
partition means in said housing including a movable member separating said first and second chambers and movable in response to the pressure differential therebetween, said movable member retaining said valve seat means.

20. A surgically implantable cerebrospinal fluid control valve as defined in claim 19 wherein said valve seat means define a fluid flow passageway of frusto-conical configuration presenting a progressively increasing diameter toward said second chamber.

21. A surgically implantable valve as defined in claim 2, wherein said orifice of said valve seat means is dimensioned to allow the passage of said restrictor means therethrough, said valve seat means being disposed between said valve closure means and said restrictor means and mounted for movement from a first position in which said valve seat means move into closing relationship with said valve closure means thereby closing said valving means, to a second position in which said restrictor means extend into said orifice of said valving means to control fluid flow therethrough.

* * * * *